United States Patent
Parari

(10) Patent No.: US 12,259,268 B2
(45) Date of Patent: Mar. 25, 2025

(54) NON-INTRUSIVE FLOW SENSOR

(71) Applicant: MOZARC MEDICAL US LLC, Minneapolis, MN (US)

(72) Inventor: Vijaya Kumar Parari, Fridley, MN (US)

(73) Assignee: MOZARC MEDICAL US LLC, Minneapolis, MN (US)

( * ) Notice: Subject to any disclaimer, the term of this patent is extended or adjusted under 35 U.S.C. 154(b) by 949 days.

(21) Appl. No.: 17/306,090

(22) Filed: May 3, 2021

(65) Prior Publication Data

US 2022/0347364 A1 Nov. 3, 2022

(51) Int. Cl.
| | |
|---|---|
| *G01F 23/26* | (2022.01) |
| *A61M 1/28* | (2006.01) |
| *A61M 1/30* | (2006.01) |
| *G01F 23/263* | (2022.01) |
| *G16H 20/40* | (2018.01) |
| *G16H 20/17* | (2018.01) |

(52) U.S. Cl.
CPC .......... *G01F 23/266* (2013.01); *A61M 1/282* (2014.02); *A61M 1/308* (2014.02); *G01F 23/263* (2013.01); *G01F 23/268* (2013.01); *G16H 20/40* (2018.01); *A61M 1/287* (2013.01); *A61M 2205/3317* (2013.01); *A61M 2205/3331* (2013.01); *A61M 2205/3334* (2013.01); *A61M 2205/3389* (2013.01); *A61M 2205/3569* (2013.01); *A61M 2205/3592* (2013.01); *G16H 20/17* (2018.01)

(58) Field of Classification Search
CPC ...... A61M 1/282; A61M 1/287; A61M 1/308; A61M 2205/3317; A61M 2205/3331; A61M 2205/3334; A61M 2205/3389; A61M 2205/3569; A61M 2205/3592; G01F 23/263; G01F 23/266; G01F 23/268; G16H 20/17; G16H 20/40
See application file for complete search history.

(56) References Cited

FOREIGN PATENT DOCUMENTS

CA 1133112 A * 10/1982

* cited by examiner

*Primary Examiner* — John Kim

(57) ABSTRACT

The disclosure relates to systems, devices, and methods for sensing the volume of liquid in a container, such as within a medical device. The systems, devices, and methods can measure the properties of a signal sent across a container using non-intrusive components that remain outside the container. The measured properties can be used to determine the volume of liquid in the container, as well as changes to the volume of liquid representing flow into and out of the container.

8 Claims, 6 Drawing Sheets

NON-INTRUSIVE FLOW SENSOR

FIELD

Systems, devices, and methods are provided for sensing a flow of liquid into and out of a container, such as a reservoir for holding a medical fluid, or any other container in which liquid is stored and released.

BACKGROUND

An amount of liquid to be held and transported into and out of a device or system is typically regulated by various sensors for proper functioning. For example, medical devices that administer fluids to patients sometimes regulate how much and how quickly the fluids are delivered. Similarly, devices that involve admixture of different components to generate a desired result regulate how much of each liquid component is included for proper mixing. The conventional devices and systems sometimes use flow sensors to aid in regulation of the liquid amounts. However, the conventional components and system often position sensors within the liquid or directly contact the liquid to measure flow. This intrusion can disturb the liquid flow itself, introducing additional turbidity and a potential source of impurities. Furthermore, the sensor may become mis-calibrated or damaged by prolonged exposure to the liquid. Hence, there is a need for a flow sensor that can non-intrusively monitor and measure a liquid and a liquid flow. There is a related need for preserving laminar and uncontaminated flow in a medical device. The need relates to the transport and delivery of a fluid such as a dialysate or blood. There is still further a need for a non-intrusive sensor that can accurately and precisely measure flow of a liquid within a device.

SUMMARY OF THE INVENTION

The first aspect relates to a system for liquid flow. In any embodiment, the system can include a container; an inflow line and an outflow line in fluid communication with the container; a flow sensor with a non-intrusive signal transmitter, a non-intrusive signal receiver, and a circuit measuring a signal from the transmitter to the receiver; and a control system receiving data from the measuring circuit. The control system can be programmed to determine a liquid volume in the container based on the received data.

In any embodiment, the control system can be programmed to determine a rate of change of the liquid volume in the container.

In any embodiment, the control system can be programmed to determine a flow rate of fluid entering from the inflow line or exiting into the outflow line based on the received data.

In any embodiment, the container can be made of a non-conductive material.

In any embodiment, the signal transmitter and the signal receiver can be made of conductive plates. The liquid volume in the container can affect the capacitance of the plates. The measuring circuit can be a capacitance sensing unit. The liquid volume can be determined according to the measured capacitance in the conductive plates.

In any embodiment, the signal transmitter and signal receiver can be RF transmission components. the liquid volume in the container can affect the impedance in an RF transmission line between the transmitter and the receiver. The measuring circuit can measure RF impedance. The liquid volume can be determined according to the measured impedance in the RF transmission line between the transmitter and the receiver.

The features disclosed as being part of the first aspect can be in the first aspect, either alone or in combination, or follow any arrangement or permutation of any one or more of the described elements. Similarly, any features disclosed as being part of the first aspect can be in a second, third, or fourth, aspect described below, either alone or in combination, or follow any arrangement or permutation of any one or more of the described elements.

The second aspect relates to a flow sensor. In any embodiment, the flow sensor can include a first conductive plate and a second conductive plate and a capacitance sensor measuring a capacitance between the first and second conductive plates that varies according to a liquid volume in a container; the first and second conductive plates both non-intrusive to the container; the capacitance sensor in communication with a control system; the control system programmed to determine the liquid volume in the container based on the capacitance.

In any embodiment, the control system can be programmed to determine a rate of change of the liquid volume in the container.

In any embodiment, the control system can be programmed to determine a flow rate of liquid entering or exiting the container based on the measured capacitance.

In any embodiment, the container can be made of a non-conductive material.

In any embodiment, the liquid can be purified water suitable for admixture with an injectable medical fluid and determining the liquid volume in the container can be based on using the dielectric properties of the purified water.

In any embodiment, the liquid can be peritoneal dialysis fluid suitable for medical injection and determining the liquid volume in the container can be based on using the dielectric properties of the peritoneal dialysis fluid.

The features disclosed as being part of the second aspect can be in the second aspect, either alone or in combination, or follow any arrangement or permutation of any one or more of the described elements. Similarly, any features disclosed as being part of the second aspect can be in the first, third, or fourth aspect described above and below, either alone or in combination, or follow any arrangement or permutation of any one or more of the described elements.

The third aspect relates to a flow sensor. In any embodiment, the flow sensor can include an RF transmission line between an RF transmitter and an RF receiver; and an RF impedance measuring circuit; the RF impedance measuring circuit measuring an RF impedance in the RF transmission line that varies with a liquid volume in a container; the RF transmitter and RF receiver both non-intrusive to the container; the RF impedance measuring circuit in communication with a control system; the control system programmed to determine a liquid volume in the container based on the measured impedance.

In any embodiment, the control system can be programmed to determine a rate of change of the liquid volume in the container.

In any embodiment, the control system can be programmed to determine a flow rate of fluid entering or exiting the container based on the RF impedance.

In any embodiment, the container can be made of a non-conductive material.

In any embodiment, the impedance measuring circuit can include a narrow bandpass filter, and the RF transmission line can carry an RF signal within a passband of the filter.

In any embodiment, the impedance measuring circuit can include an operational amplifier.

In any embodiment, the liquid can be purified water suitable for admixture with an injectable medical fluid; and determining the liquid volume in the container can be based on the dielectric properties of the purified water.

In any embodiment, the liquid can be peritoneal dialysis fluid suitable for medical injection; and determining the liquid volume in the container can be based on the dielectric properties of the peritoneal dialysis fluid.

The features disclosed as being part of the third aspect can be in the third aspect, either alone or in combination, or follow any arrangement or permutation of any one or more of the described elements. Similarly, any features disclosed as being part of the third aspect can be in the first, second, or fifth aspect, either alone or in combination, or follow any arrangement or permutation of any one or more of the described elements.

The fourth aspect relates to a peritoneal dialysis system including a flow sensor.

In any embodiment, the container can be a purified water container fluidly connected to a water purification module.

In any embodiment, the purified water container can be fluidly connected to a peritoneal dialysis fluid generation system.

In any embodiment, the control system can be programmed to control one or more pumps and/or one or more valves to pump a specified volume of purified water from the purified water container through the peritoneal dialysis fluid generation system to generate a peritoneal dialysis fluid based on a flow rate of water exiting the purified water container.

In any embodiment, the container can be a peritoneal dialysis fluid container fluidly connected to a peritoneal dialysis fluid generation system.

In any embodiment, the control system can be programmed to control one or more pumps and/or one or more valves to pump a specified volume of peritoneal dialysis fluid into a peritoneal cavity of a patient based on a flow rate of the fluid exiting the peritoneal dialysis fluid container.

In any embodiment, the control system can be programmed to control one or more pumps and/or one or more valves to pump a specified volume of fluid from the peritoneal dialysis fluid generation system into the peritoneal dialysis fluid container based on a flow rate of the fluid entering the peritoneal dialysis fluid container.

The features disclosed as being part of the fourth aspect can be in the fourth aspect, either alone or in combination, or follow any arrangement or permutation of any one or more of the described elements. Similarly, any features disclosed as being part of the fourth aspect can be in the first, second, or third aspect, either alone or in combination, or follow any arrangement or permutation of any one or more of the described elements.

DETAILED DESCRIPTION

Figure 1:
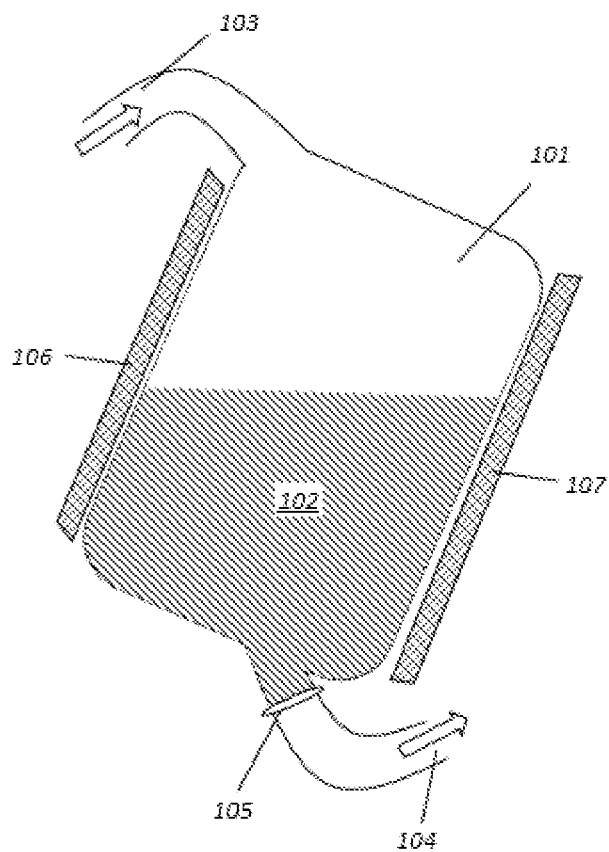
FIG. 1 is a cross-sectional view of a liquid container with a non-intrusive flow sensor.

Unless defined otherwise, all technical and scientific terms used have the same meaning as commonly understood by one of ordinary skill in the art.

The articles "a" and "an" are used to refer to one to over one (i.e., to at least one) of the grammatical object of the article. For example, "an element" means one element or over one element.

To "associate" means to identify one piece of information as related to a second piece of information.

A "capacitor" is an arrangement of elements within an electric circuit that hold an electric charge. Each capacitor includes a pair of conductive plates and has a characteristic capacitance.

The terms "communication," "communicate," "communicating," and the like can refer to the ability to transmit electronic data, instructions, information wirelessly, via direct electrical connection, or any other electrical transmission means between one or more components.

The term "compare" means to determine whether two files or data are the same or different.

The term "comprising" includes, but is not limited to, whatever follows the word "comprising." Use of the term indicates the listed elements are required or mandatory but that other elements are optional and may be present.

A "conductive plate" is any element that acts as a capacitor within a circuit. No particular limits or thresholds to conductance are required for a component to be a "conductive plate," provided that the element acts as a capacitor.

The term "consisting of" includes and is limited to whatever follows the phrase "consisting of." The phrase indicates the limited elements are required or mandatory and that no other elements may be present.

The term "consisting essentially of" includes whatever follows the term "consisting essentially of" and additional elements, structures, acts or features that do not affect the basic operation of the apparatus, structure or method described.

The term "device," as used herein, refers to any device that can authenticate a user or USB authentication device.

The term "determining" or to "determine" refers to ascertaining a particular state of a component or system.

The term "device" is to be interpreted in the broadest and can include anything made for a particular purpose, a contrivance of any type, particularly a mechanical or electrical component or hardware. Some examples of devices can include a medical device such as a dialysis machine, laptop, computer, computer peripherals of any type, computer terminals, portable devices, smart phones, and smart watches.

A "dialysis system" is a collection of medical devices used to provide dialysis treatment of any type including hemodialysis, peritoneal dialysis, ultrafiltration and hemodiafiltration and the like to one or more patients.

The term "execute" means to perform a step or series of steps.

The term "fluid communication" means that two chambers are connected, either directly or indirectly, with or without intervening elements such as valves, membranes, stoppers, or the like, so that fluid flows from one chamber into another. Chambers are in "fluid communication" whether or not the fluid flows in both directions.

A component is "intrusive" if the component is positioned within a chamber for holding or transporting liquid such that the component will come in physical contact with the liquid.

The term "medical device" refers to a device used to perform medical treatment or diagnosis of any type.

To "measure" is to determine a quantifiable property of a component or system via a sensor.

The term "non-intrusive" describes any system, device, or component if any feature of the system, device, or component used to implement the method are positioned outside of the chambers where liquid is transported and stored so that none of the components come in physical contact with the measurand, such as a liquid.

A "peritoneal dialysis system" is a collection of medical devices used to provide peritoneal dialysis treatment to a patient.

The term "peritoneal dialysis fluid" refers to the mixture that is injected into a patient during peritoneal dialysis treatment. When properties of peritoneal dialysis fluid are described herein, such as its dielectric properties and permittivity, they refer to the properties of the fluid before its use in treatment.

The term "programmed" can mean a series of instructions that cause a device or system to perform certain steps.

The term "receiving" refers to the process of obtaining electronic information by any means.

An "RF transmission line" is a path between an RF transmitter and an RF receiver over which a radio frequency signal is transmitted. The path need not be a straight line between the components. Reflection, refraction, induction, and other effects that modify the RF signal during its transmission are part of the RF transmission line.

The term "sending" refers to the process of transmitting electronic information to be received.

A "sensor" is a device configured to determine a particular state of a component, substance, or component whether in a system or not. For example, a sensor can measure a liquid, a flow rate, and the like.

A "signal" is a distinct arrangement of data, matter, and/or energy sent over a medium by a transmitter that is recognized by a receiver. Transmitted energy is a "signal" regardless of whether the energy includes any particularized data.

Non-Intrusive Flow Sensor

FIG. 1 shows a container 101 disposed within a flow path for a liquid 102. Liquid moves from an inlet 103 to an outlet 104; the outlet is blocked by a valve 105 that can be selectively opened to allow the liquid 102 to be dispensed or held in the container. To measure the volume of liquid 102 in the container 101, a pair of conductive plates 106 and 107 can be placed adjacent the container 101 but outside the walls so as not to contact the liquid 102. The conductive plates 106 and 107 are non-intrusive with respect to the flow of the liquid 102 in the container 101: they do not physically contact the liquid 102 or divert the fluid path. The plates 106 and 107 can form a capacitor within a circuit which has additional components such that the capacitance between the two plates 106, 107, can be accurately measured; for instance, the circuit can include a resistor and/or inductor of known electrical properties. When a known quantity of current is passed through the circuit, the change in voltage will be proportional to the capacitance between the plates, thus providing that measurement to the circuit.

Figure 2:
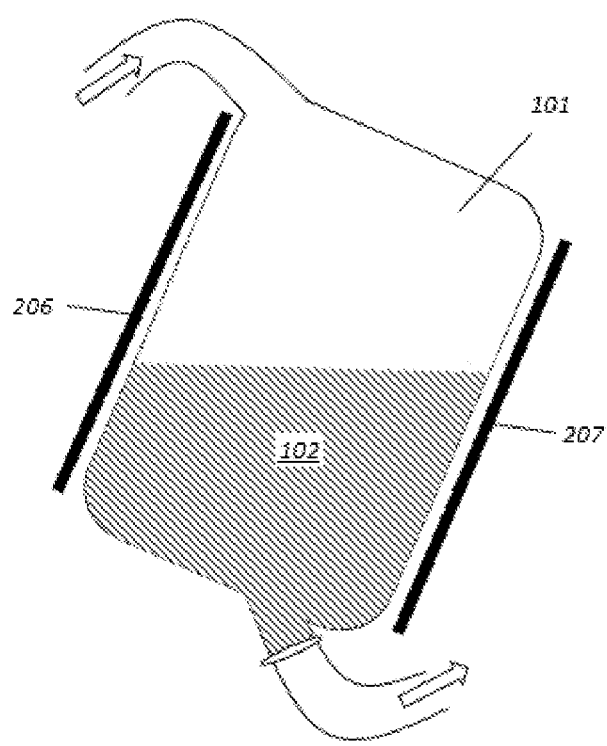
FIG. 2 is a cross-sectional view of a liquid container with a non-intrusive flow sensor.

FIG. 2 illustrates a sensor embodiment in which the conductive plates 206 and 207 forms the RF waveguide which act as a level sensor, The RF transmitter, receiver, and wave guide and liquid medium filled between the waveguide plates form parts of a circuit capable of generating an RF signal and then measuring the loss when the signal is received, thus allowing measurement of the impedance across the RF transmission line.

Figure 3:
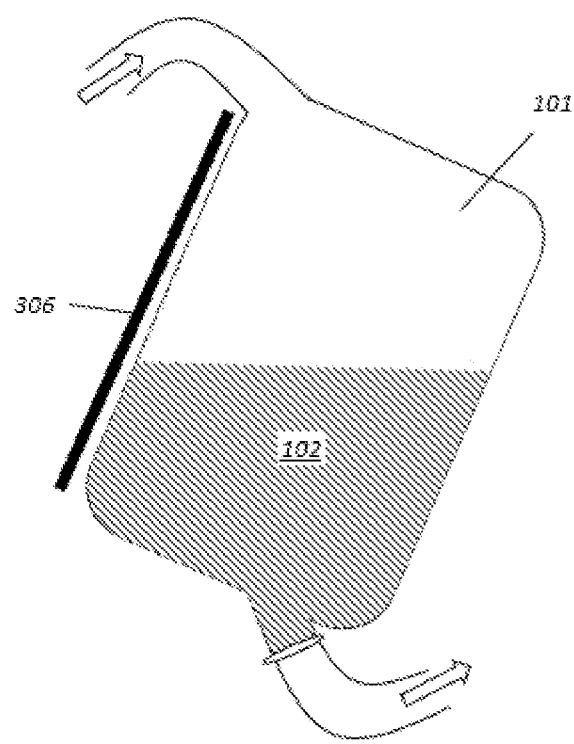
FIG. 3 is a cross-sectional view of a liquid container with a non-intrusive flow sensor.

FIG. 3 illustrates a sensor embodiment in which a single RF wave guide made of parallel conductor plates 306 acts as a level sensor, measuring a reflected signal by means of reflectometry included in the sensor circuit. As with the two-conductor waveguide system above, the circuit generates an RF signal and then measures the loss when the signal is received, thus allowing measurement of the impedance across the RF transmission line.

Because water and aqueous solutions have significantly different dielectric properties than air, the measured capacitance or impedance can be used to calculate the volume of liquid found in the container through which the signal is transmitted. For example, parallel conductive plates have a characteristic capacitance of:

$$C = \varepsilon_0 * \varepsilon_r * A/d$$

Where A and d are the area of and distance between the plates and $\varepsilon_0$ is the permittivity of the free space between the plates and $\varepsilon_r$ is the permittivity of water. Since $\varepsilon_r$ of water is $>> \varepsilon_0$, the capacitance of the level sensor can be approximated to capacitance formed because of level of water.

Knowing the geometry of the sensor elements and the dielectric properties of the liquid, the change in the volume of the liquid can be determined based on detecting a change in the capacitance:

$$\Delta V_{liquid} = \Delta C$$

The impedance of an RF wave can be similarly determined wherein impedance depends on the permittivity of the medium as well, particularly:

$$Z^2 = \mu/\varepsilon$$

For the impedance Z of a wave travelling through a non-conductive medium of permeability $\mu$ and permittivity $\varepsilon$. For water and other aqueous substances with negligible magnetic properties (those that have a relative permeability $\mu$ of approximately 1), the permeability of free space can be used. For a change in the volume of liquid in the container, then, the change of impedance would be:

$$\Delta Z = \sqrt{(\mu_0 (\varepsilon_{air} - \varepsilon_{liquid}) \Delta V [\varepsilon^2 - (\varepsilon_{air} - \varepsilon_{liquid}) \Delta V])}$$

which, in cases where the change in permittivity due to the change in volume would represent a small portion of the overall permittivity of the space, approximates to:

$$\Delta Z = \sqrt{(\mu_0 (\varepsilon_{air} - \varepsilon_{liquid}) \Delta V)} / \varepsilon$$

Therefore, if the overall permittivity $\varepsilon$ of the transmission line is known, as well as the difference in permittivity between the liquid in the container and the air, a change in volume can be calculated as proportional to the square of the change in impedance:

$$\Delta V = \Delta Z^2 * \varepsilon^2 / (\mu_0 (\varepsilon_{air} - \varepsilon_{liquid}))$$

These equations can therefore be used to find V, the amount of liquid in the container, or $\Delta V$, the amount of water entering or leaving the container. If measurements are recorded and taken over time, a rate of change of the volume, representing a flow rate either into or out of the container, could also be calculated.

Figure 4:
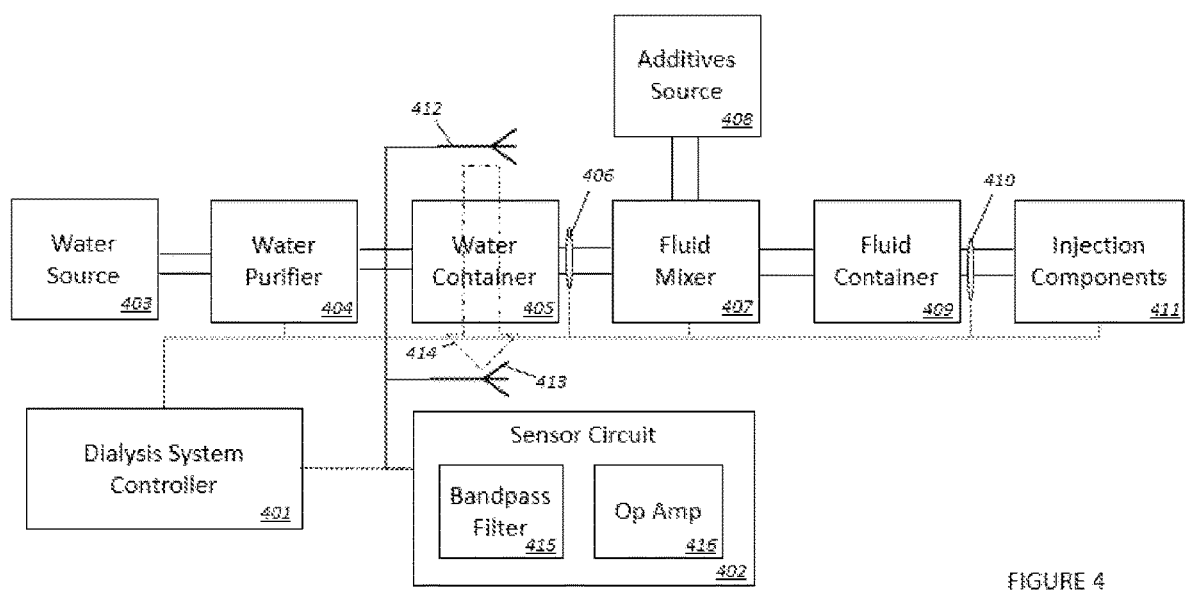
FIG. 4 is a diagram of a dialysis system including a non-intrusive flow sensor.
Figure 5:
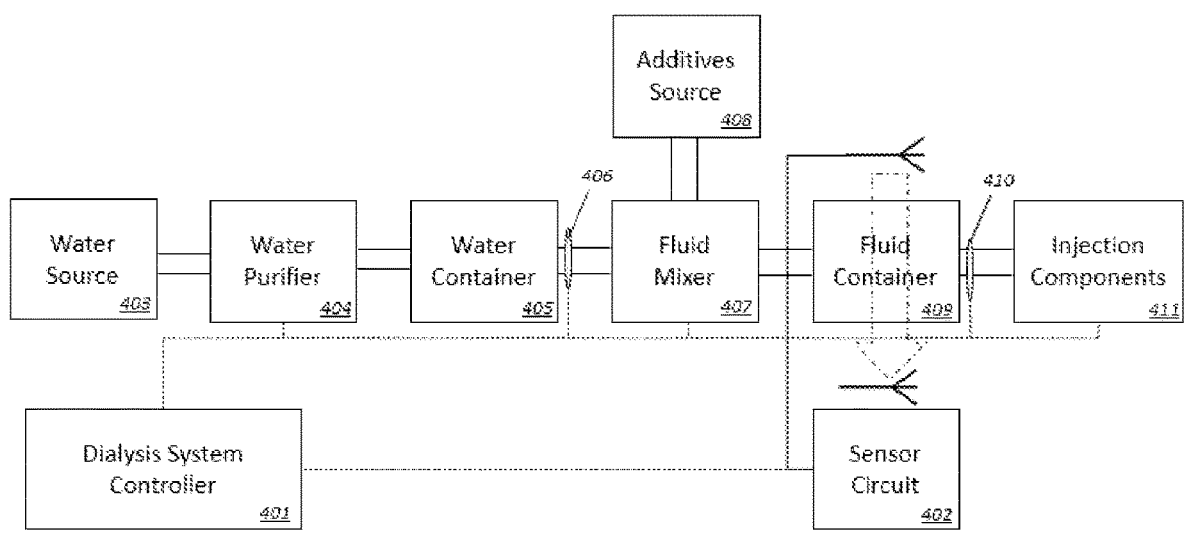
FIG. 5 is a diagram of a dialysis system including a non-intrusive flow sensor.

FIGS. 4 and 5 are component diagrams showing a dialysis system 400 that includes a non-intrusive flow sensor as described herein. Components can be connected by double lines to show fluid communication. A dialysis system controller's electronic communication connection is illustrated by dotted lines; the dialysis system controller 401 sends control signals to many components as well as receiving data from a sensor circuit 402.

As shown, water passes from a water source 403 to a water purifier 404. The water source 403 can represent pretreated water, and part of the function of the water purifier 404 can be assuring that water received from the water source 403 is suitable for purification by the system. In some embodiments, the water source 403 can be a commercially or residentially available water supply, such as tap water. The dialysis system controller 401 can send control signals to the water purifier 404 and can also receive signals when certain operations, such as a water purification process, have completed.

Purified water can be held in a water container 405, which as described above can include an outlet valve 406 to regulate when and at what rate the water is dispensed. The water container 405 can be made of any appropriate material and can be rigid or deformable. In some embodiments, the container 405 can be a fully modular component of the system 400, so that a user can swap a damaged or malfunctioning container with a similar container.

Water dispensed from the container 405 enters a mixer 407 where the water is combined with additives from an additives source 408 to form a dialysis fluid. Where the dialysis system 400 is used for peritoneal dialysis, the fluid mixer 407 is calibrated to produce a peritoneal dialysis fluid appropriate for injection into a patient as part of a peritoneal dialysis procedure. The dialysis system controller 401 sends instructions to the mixer 407 to create fluid, which can depend on the rate at which water is dispensed from the water container 405.

The peritoneal dialysis fluid is stored in a fluid container 409, which can again have an outlet valve 410 controlled by the dialysis system controller 401 to determine when and at what rate the fluid is dispensed. The properties of the fluid container 409 can be similar to those of the water container 405 or can vary according to the different needs of the two steps in the treatment process; for instance, the overall capacity of the containers can be different, they can be of different geometries to accommodate other components of the device, or they can be made of the different materials to best hold their associated liquid. Upon operation of the valve 410 by the dialysis system controller 401, the peritoneal dialysis fluid is dispensed to injection components 411 in accordance with the dialysis treatment.

As shown in FIG. 4, the sensor circuit 402 can be in communication with a transmitter element 412 and receiver element 413 for sending a signal 414 through the water container 405 to measure the dielectric properties of the container. The measurements taken by the sensor circuit 402 (which can include capacitance and/or impedance, as described above, but may also include further quantities depending on the specific construction of the circuit, such as inductance, voltage, current, resistance, signal strength, signal frequency, and/or others) are communicated to the dialysis system controller 401 to determine the volume of the water container 405.

Many components of electrical circuits known in the art can be included in the sensor circuit 402. For example, a bandpass filter 415 can be included in the sensor circuit 402, isolating the signal 414 from signals outside the passband permitted by the filter. Furthermore, any suitable operational amplifier 416 can be used to boost the received signal to ensure that a usable measurement reaches the dialysis system controller 401.

Similar elements are shown in FIG. 5, except that the sensor circuit 402 is shown around the fluid container 409.

The permittivity and other dielectric properties of peritoneal dialysis fluid, rather than of water, will be used to calculate the volume of water available in the container 409. Any of the circuitry components discussed above can be used to support the measurement process for the sensor circuit 402. The volume of fluid in the container, and/or the flow rate into and out of the container, can be used in determining when and at what rate to dispense the peritoneal dialysis fluid to the injection components 411.

Although FIGS. 4 and 5 illustrate alternative embodiments in which a sensor circuit 402 is deployed at one of two containers, in another embodiment, multiple sensor circuits could be used to measure multiple containers within the same system. The sensors could be the same or could vary one from another, including any of the variations described herein or understood in the art. Any number of sensor circuits could be in communication with the same or multiple different controllers of a medical treatment system to best monitor and operate the devices.

Usage of Non-Intrusive Flow Sensor

Figure 6:
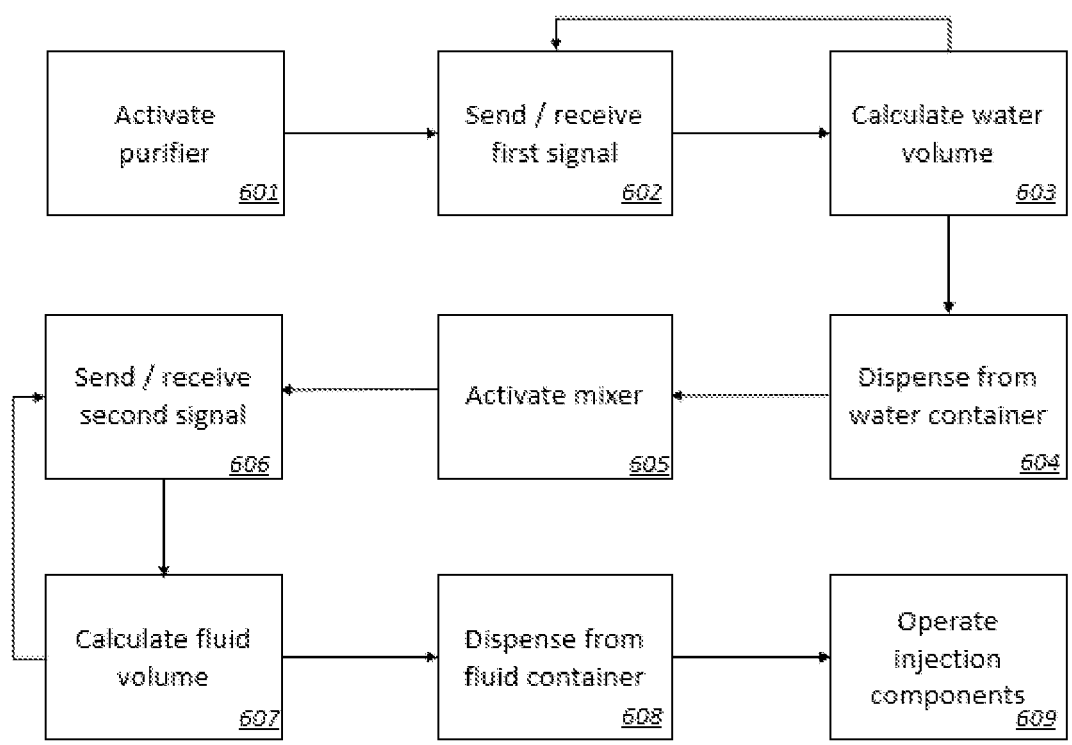
FIG. 6 is a flow chart showing steps for operating a dialysis system including the use of non-intrusive flow sensors to monitor liquid volumes in containers.

FIG. 6 is a flow chart showing a method for controlling a dialysis system in conjunction with non-intrusive flow sensors as described herein. As briefly described above, this method describes steps in which both a water container and a fluid container are measured by flow sensors; either of these steps could be taken without the others in the case where only one of the sensor circuits is employed or currently active.

In step 601, the water purifier is activated. This can involve receiving water from a water source, which can be pumped or otherwise controlled. The purifier dispenses water into a water container, where the water is held for controlled dispensation during subsequent steps.

In step 602, a first signal is sent and received from a sensor circuit positioned to monitor the water container. Then, in step 603, the system controller calculates the volume of the water from the measurements associated with the sent/received signals. In some embodiments, this monitoring process can begin as soon as the dialysis system begins and can continue if there is water left to purify and/or store in the water container. The calculated water volume can include, not only the approximate total volume in the container, but also the rate at which the container is gaining water from the purifier.

In step 604, the system dispenses water from the container. The timing and flow rate of the water dispensed from the water container can depend on the quantities calculated in steps 603, above. When sufficient water is dispensed, in step 605, the system can activate the mixer. Properly mixed dialysis fluid, produced from rates regulated by the system controller, enters the dialysis fluid container from the mixer during this step.

Steps 606 and 607 comprise a second set of monitoring steps positioned at the fluid container. These steps can begin with the original activation of the device or with activation of the mixer and can continue if sufficient fluid remains in the fluid container to measure the volume and/or flow. Again, the calculated volume can include flow quantities as well as total volume of fluid available, and the calculations of step 607 consider the dielectric properties of the fluid mixture as they differ from water.

In step 608, the system dispenses fluid from the dialysis fluid container, which can depend on the calculated rates of flow and/or total volume available in the container. In step 609, the quantity and rate of available fluid can also determine when and how the injection components are operated by the system controller. For example, injection rates can be limited based on how much fluid is calculated to be ready for injection, and the system cannot begin certain steps of treatment at all until sufficient quantities of fluid are available.

One skilled in the art will understand that various combinations and/or modifications and variations can be made in the described systems and methods depending upon the specific needs for operation. Various aspects disclosed herein can be combined in different combinations than the combinations specifically presented in the description and accompanying drawings. Moreover, features illustrated or described as being part of an aspect of the disclosure can be used in the aspect of the disclosure, either alone or in combination, or follow a preferred arrangement of one or more of the described elements. Depending on the example, certain acts or events of any of the processes or methods described herein can be performed in a different sequence, can be added, merged, or left out altogether (e.g., certain described acts or events cannot be necessary to carry out the techniques). In addition, while certain aspects of this disclosure are described as performed by a single module or unit for purposes of clarity, the techniques of this disclosure can be performed by a combination of units or modules associated with, for example, a device.

What is claimed is:

1. A flow sensor, comprising:
an RF transmission line between an RF transmitter and an RF receiver; and
an RF impedance measuring circuit; the RF impedance measuring circuit measuring an RF impedance in the RF transmission line that varies with a liquid volume in a container; the RF transmitter and RF receiver both non-intrusive to the container;
the RF impedance measuring circuit in communication with a control system; the control system programmed to determine a liquid volume in the container based on the measured impedance.

2. The flow sensor of claim 1, the control system programmed to determine a rate of change of the liquid volume in the container.

3. The flow sensor of claim 1, the control system programmed to determine a flow rate of fluid entering or exiting the container based on the RF impedance.

4. The flow sensor of claim 1, wherein the container is made of a non-conductive material.

5. The flow sensor of claim 1, the impedance measuring circuit including a narrow bandpass filter, the RF transmission line carrying an RF signal within a passband of the filter.

6. The flow sensor of claim 1, the impedance measuring circuit including an operational amplifier.

7. The flow sensor of claim 1, wherein:
the liquid is purified water suitable for admixture with an injectable medical fluid; and
determining the liquid volume in the container is based on the dielectric properties of the purified water.

8. The flow sensor of claim 1, wherein:
the liquid is peritoneal dialysis fluid suitable for medical injection; and
determining the liquid volume in the container is based on the dielectric properties of the peritoneal dialysis fluid.

* * * * *